(12) United States Patent
Morita

(10) Patent No.: US 11,805,983 B2
(45) Date of Patent: Nov. 7, 2023

(54) OPTICAL PATH DEFLECTING PRISM FOR ENDOSCOPE, OBLIQUE-VIEWING ENDOSCOPE OPTICAL SYSTEM HAVING THE SAME AND ENDOSCOPE

(71) Applicant: OLYMPUS CORPORATION, Hachioji (JP)

(72) Inventor: Kazuo Morita, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 599 days.

(21) Appl. No.: 17/020,966

(22) Filed: Sep. 15, 2020

(65) Prior Publication Data

US 2021/0068633 A1 Mar. 11, 2021

Related U.S. Application Data

(63) Continuation of application No. PCT/JP2019/009710, filed on Mar. 11, 2019.

(30) Foreign Application Priority Data

Apr. 2, 2018 (JP) .................................. 2018-070643

(51) Int. Cl.
*A61B 1/00* (2006.01)
*G02B 5/04* (2006.01)
*G02B 23/24* (2006.01)

(52) U.S. Cl.
CPC ...... *A61B 1/00179* (2013.01); *A61B 1/00163* (2013.01); *A61B 1/00174* (2013.01);
(Continued)

(58) Field of Classification Search
CPC ............ A61B 1/00179; A61B 1/00096; A61B 1/0623; A61B 1/00172; A61B 1/00;
(Continued)

(56) References Cited

U.S. PATENT DOCUMENTS 4,138,192 A * 2/1979 Yamasita ........... G02B 23/2423
359/834
4,783,156 A 11/1988 Yokota
(Continued)

FOREIGN PATENT DOCUMENTS

JP S62179716 U 11/1987
JP H08082766 A 3/1996
(Continued)

OTHER PUBLICATIONS

International Search Report (ISR) (and English language translation thereof) dated Jun. 11, 2019, issued in International Application No. PCT/JP2019/009710.
(Continued)

*Primary Examiner* — Ryan N Henderson
*Assistant Examiner* — Sung Ham
(74) *Attorney, Agent, or Firm* — Holtz, Holtz & Volek PC

(57) ABSTRACT

An optical path deflecting prism for endoscope which is used for observing an object in an oblique direction, includes a first prism and a second prism, and the first prism and the second prism are cemented. The first prism has a first polished surface and a second polished surface. The first reflecting surface is a mirror surface having a mirror coating applied to a polished surface of a flat plate, and is fixed by gluing to the fifth polished surface of the second prism upon adjusting an angle so as to correct an optical-axis shift which occurs due to a manufacturing error of the first prism and the second prism.

3 Claims, 13 Drawing Sheets

(52) U.S. Cl.
CPC ...... *A61B 1/00181* (2013.01); *A61B 1/00183* (2013.01); *G02B 5/04* (2013.01); *G02B 23/243* (2013.01)

(58) Field of Classification Search
CPC ............ A61B 1/00181; A61B 1/00183; G02B 5/04; G02B 23/2423; G02B 23/243
See application file for complete search history.

(56) References Cited

U.S. PATENT DOCUMENTS

| | | | |
|---|---|---|---|
| 5,689,365 | A | 11/1997 | Takahashi |
| 9,474,439 | B2 | 10/2016 | Baumann et al. |
| 2002/0091305 | A1* | 7/2002 | Lederer ............ G02B 23/2423 600/176 |
| 2013/0176638 | A1* | 7/2013 | Schouwink .......... G02B 23/243 359/834 |
| 2014/0135577 | A1 | 5/2014 | Baumann et al. |
| 2017/0003582 | A1* | 1/2017 | Pan ...................... G03B 21/008 |
| 2018/0055341 | A1* | 3/2018 | Tuscher ................. A61B 1/055 |
| 2018/0143421 | A1* | 5/2018 | Hegenbarth ............. G02B 3/00 |
| 2018/0360298 | A1* | 12/2018 | Khettal ............. A61B 1/00179 |

FOREIGN PATENT DOCUMENTS

| | | | |
|---|---|---|---|
| JP | 09288240 | A * | 11/1997 |
| JP | H09288240 | A | 11/1997 |
| JP | H10123411 | A | 5/1998 |
| JP | 2006039259 | A | 2/2006 |

OTHER PUBLICATIONS

Written Opinion dated Jun. 11, 2019, issued in International Application No. PCT/JP2019/009710.

International Preliminary Report on Patentability (IPRP) (and English language translation thereof) dated Oct. 15, 2020 issued in International Application No. PCT/JP2019/009710.

* cited by examiner

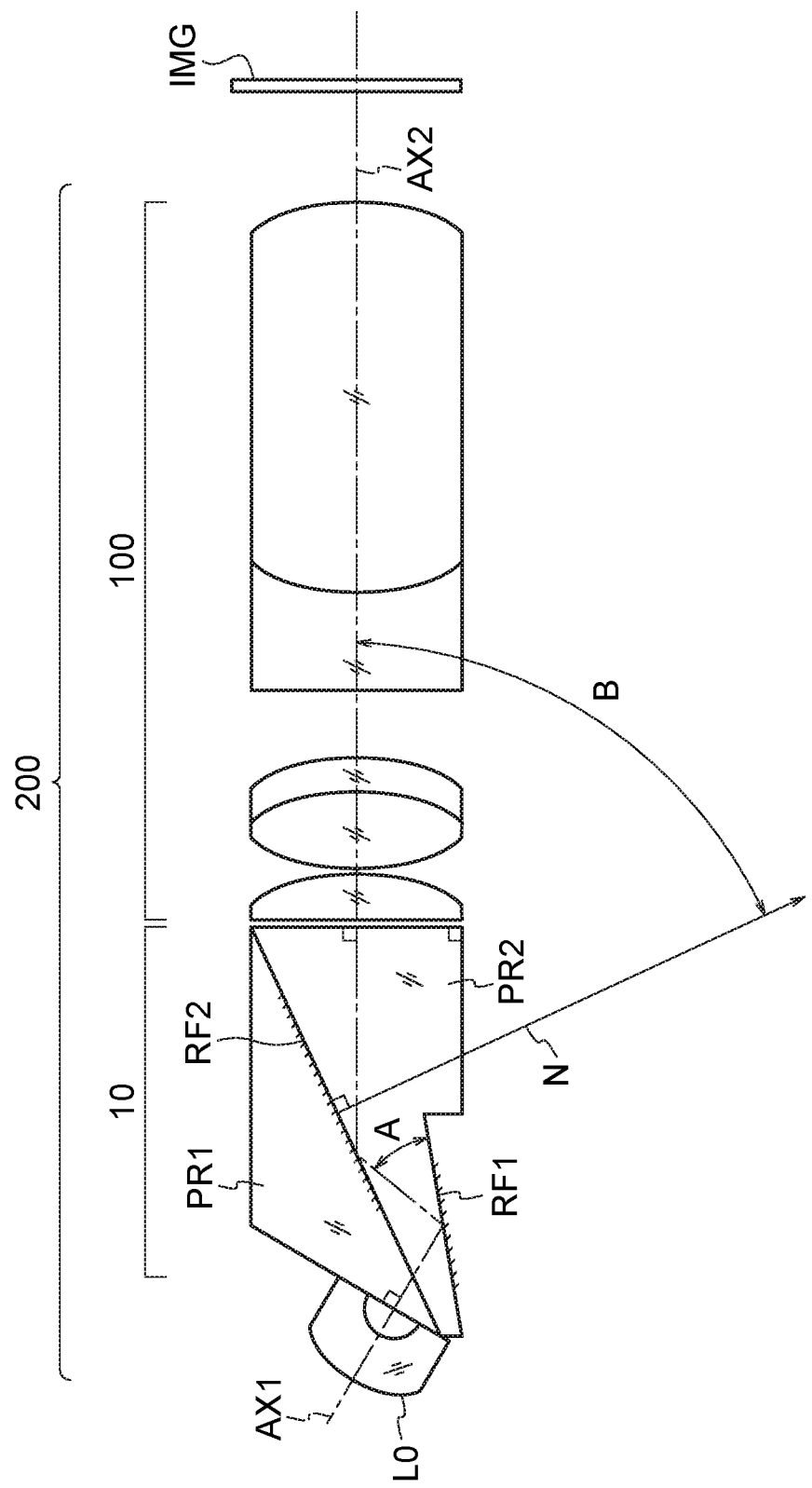

OPTICAL PATH DEFLECTING PRISM FOR ENDOSCOPE, OBLIQUE-VIEWING ENDOSCOPE OPTICAL SYSTEM HAVING THE SAME AND ENDOSCOPE

CROSS-REFERENCE TO RELATED APPLICATION

The present application is a continuation of PCT/JP2019/009710, filed on Mar. 11, 2019 which is based upon and claims the benefit of priority from Japanese Patent Application No. 2018-070643 filed on Apr. 2, 2018; the entire contents of which are incorporated herein by reference.

BACKGROUND

Technical Field

The present disclosure relates to an optical path deflecting prism for endoscope, an oblique-viewing endoscope optical system having the same and an endoscope.

Description of the Related Art

As for endoscopes for observing various parts inside a body cavity, oblique-viewing endoscopes having an optical path deflecting prism group for directing a visual-field direction in a predetermined direction have been proposed in Japanese Patent Application Laid-open Publication No. Hei 09-123411 and U.S. Pat. No. 4,138,192 Specification for example.

Moreover, a visual-field direction changing optical system has been proposed in Japanese Patent Application Laid-open Publication No. Hei 09-288240.

SUMMARY

An optical path deflecting prism for endoscope according to at least some embodiments of the present disclosure is an optical path deflecting prism for endoscope which is used for observing an object in an oblique direction.

The optical path deflecting prism for endoscope includes
a first prism, and
a second prism, wherein
the first prism and the second prism are cemented,
the first prism has a first polished surface and a second polished surface,
the first polished surface is perpendicular to an oblique direction and has a first light-beam incident surface for light incident on the optical path deflecting prism for endoscope,
the second polished surface is disposed at an angle with respect to the first polished surface, and is a cemented surface with the second prism,
the second prism has a third polished surface, a fourth polished surface, and a fifth polished surface,
the third polished surface is a cemented surface with the first prism,
the fourth polished surface is perpendicular to an optical axis of a lens group disposed on an emergence side of the optical path deflecting prism for endoscope, and is a last light-beam emergence surface for light emerged from the optical path deflecting prism for endoscope,
the fifth polished surface is disposed at an angle with respect to the third polished surface,
a first reflecting surface reflects first time a light beam incident on the optical path deflecting prism for endoscope, and exists on the fifth polished surface of the second prism,
a second reflecting surface reflects second time a light beam incident on the optical path deflecting prism for endoscope, and exists on any one of the second polished surface of the first prism and the third polished surface of the second prism,
the first reflecting surface is a mirror surface having a mirror coating applied to a polished surface of a flat plate, and
the first reflecting surface is fixed by gluing to the fifth polished surface of the second prism upon adjusting an angle so as to correct an optical-axis shift which occurs due to a manufacturing error of the first prism and the second prism.

Moreover, an oblique-viewing endoscope optical system according to at least some embodiments of the present disclosure includes the abovementioned optical path deflecting prism for endoscope, and an optical system which is disposed on an emergence side of the optical path deflecting prism for endoscope.

Furthermore, an endoscope according to at least some embodiments of the present disclosure includes the abovementioned oblique-viewing endoscope optical system.

BRIEF DESCRIPTION OF THE DRAWINGS

FIG. 2 is a cross-sectional view of a lens arrangement in an oblique-viewing endoscope optical system according to the first embodiment;

DETAILED DESCRIPTION

Reasons for and effects of adopting such arrangements for an optical path deflecting prism for endoscope according to the present embodiment, an oblique-viewing endoscope optical system having the optical path deflecting prism for endoscope, and an endoscope will be described below by using the accompanying diagrams. However, the present invention is not restricted to the embodiments described below.

First Embodiment

Figure 1A:
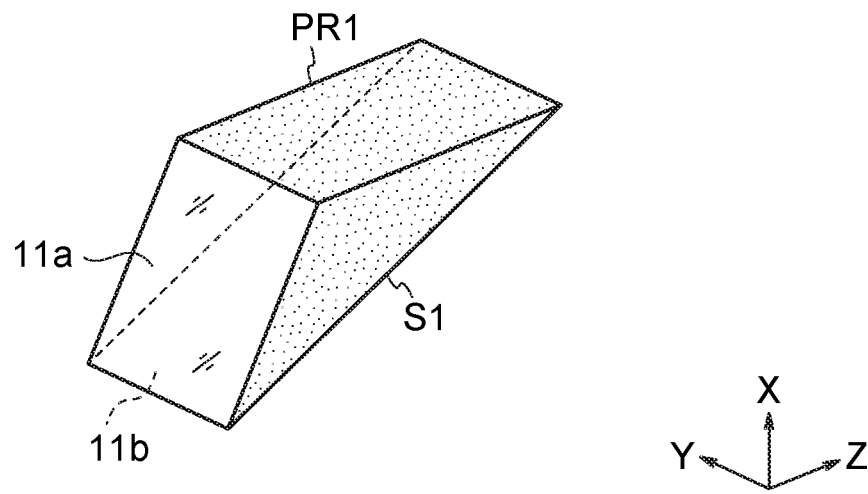
FIG. 1A is a perspective view of a first prism in an optical path deflecting prism for endoscope according to a first embodiment.
Figure 1B:
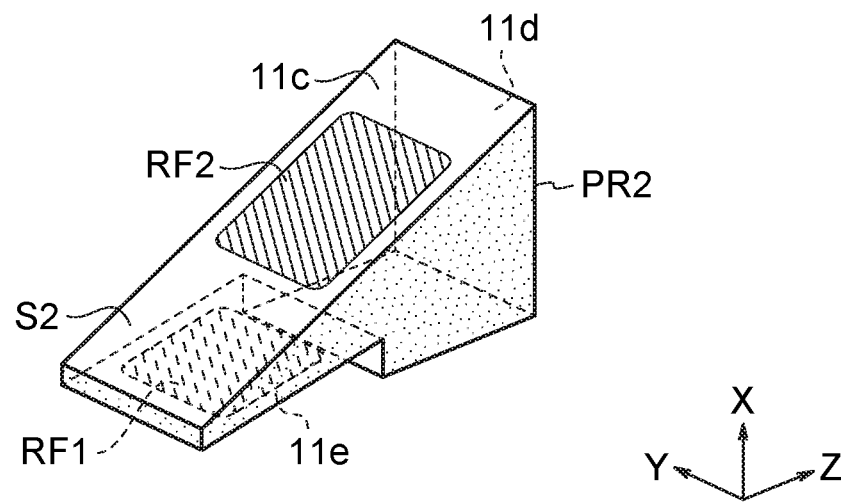
FIG. 1B is a perspective view of a second prism in the optical path deflecting prism for endoscope according to the first embodiment.
Figure 1C:
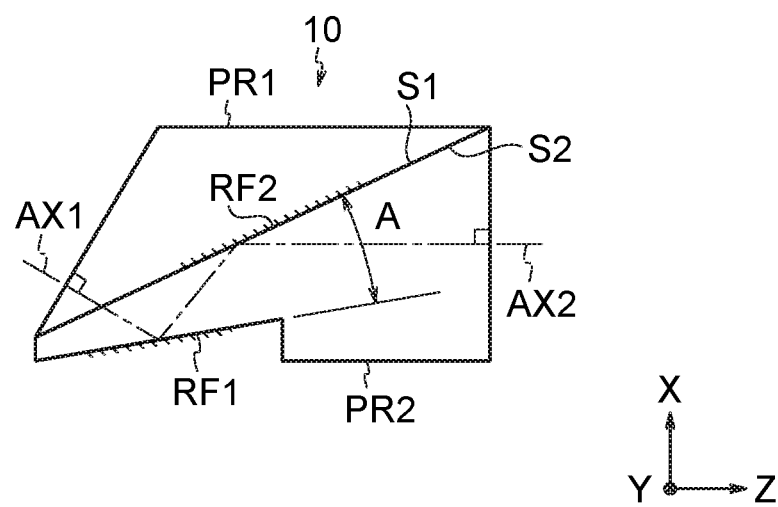
FIG. 1C is a cross-sectional view of the optical path deflecting prism for endoscope according to the first embodiment.

FIG. 1A is a perspective view of a first prism PR1 in an optical path deflecting prism for endoscope 10 according to a first embodiment. FIG. 1B is a perspective view of a second prism PR2 in the optical path deflecting prism for endoscope 10 according to the first embodiment. FIG. 1C is a cross-sectional view of the optical path deflecting prism for endoscope 10 according to the first embodiment.

The optical path deflecting prism for endoscope 10 according to the first embodiment is used for observation of an object (not shown in the diagram) in an oblique direction. The optical path deflecting prism for endoscope 10 is formed by cementing the first prism PR1 and the second prism PR2. The first prism PR1 has a first polished surface 11a which is a first light-beam incident surface for light incident on the optical path deflecting prism for endoscope 10, perpendicular to an oblique direction AX1 (FIG. 2), and a second polished surface 11b which is disposed at an angle with respect to the first polished surface 11a, and is a cemented surface with the second prism PR2. The second prism PR2 has a third polished surface 11c which is a cemented surface with the first prism PR1. The second prism PR2 has a fourth polished surface 11d which is perpendicular to an optical axis AX2 of a lens group 100 (FIG. 2) disposed on an emergence side of the optical path deflecting prism for endoscope 10, and is a last light-beam emergence surface for light emerged from the optical path deflecting prism for endoscope 10. The second prism PR2 has a fifth polished surface 11e which is disposed at an angle with respect to the third polished surface 11c. A first reflecting surface RF1 at which a light beam incident on the optical path deflecting prism for endoscope 10 is reflected first time, exists on the fifth polished surface 11e of the second prism PR2. A second reflecting surface RF2 at which a light beam incident on the optical path deflecting prism for endoscope 10 is reflected second time, exists on any one of the second polished surface 11b of the first prism PR1 and the third polished surface 11c of the second prism PR2. The following conditional expressions (1) and (2) are satisfied, $$14.5 \leq A(°) \leq 23 \quad (1)$$

$$62 \leq B(°) \leq 66 \quad (2)$$

where,

A denotes a first angle made by the first reflecting surface RF1 and the second reflecting surface RF2 with each other (FIG. 2), and B denotes a second angle made by a normal direction N of the second reflecting surface RF2 and a direction of the optical axis AX2 of the lens group 100 disposed on an emergence side of a light beam of the optical path deflecting prism for endoscope 10 (FIG. 2).

A surface S1 of the first prism PR1 shown in FIG. 1A and a surface S2 of the second prism PR2 shown in FIG. 1B are cemented. Accordingly, the optical path deflecting prism for endoscope 10 shown in FIG. 1C is formed.

FIG. 2 is a cross-sectional view of a lens arrangement in an oblique-viewing endoscope optical system 200 having the optical path deflecting prism for endoscope 10. A lens L0 is cemented to a surface of incidence of a light beam on the optical path deflecting prism for endoscope 10. An image of an object in an oblique direction (direction of the optical axis AX1) is formed on an image pickup surface of an image sensor IMG disposed on an emergence (image plane) side of the oblique-viewing endoscope optical system 200.

Moreover, it is desirable that the present embodiment satisfies conditional expression (1). Conditional expression (1) regulates an appropriate range of the first angle A.

Figure 3A:
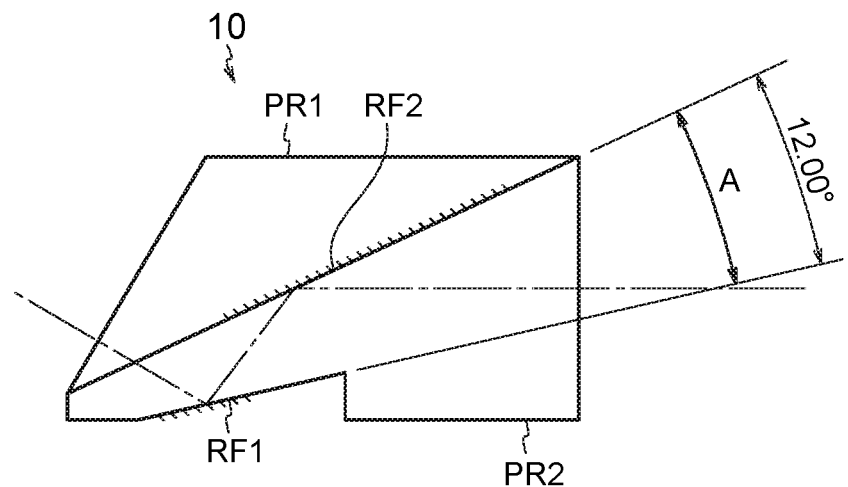
FIG. 3A, FIG. 3B, and FIG. 3C are cross-sectional views of the optical path deflecting prism according to the first embodiment.
Figure 3B:
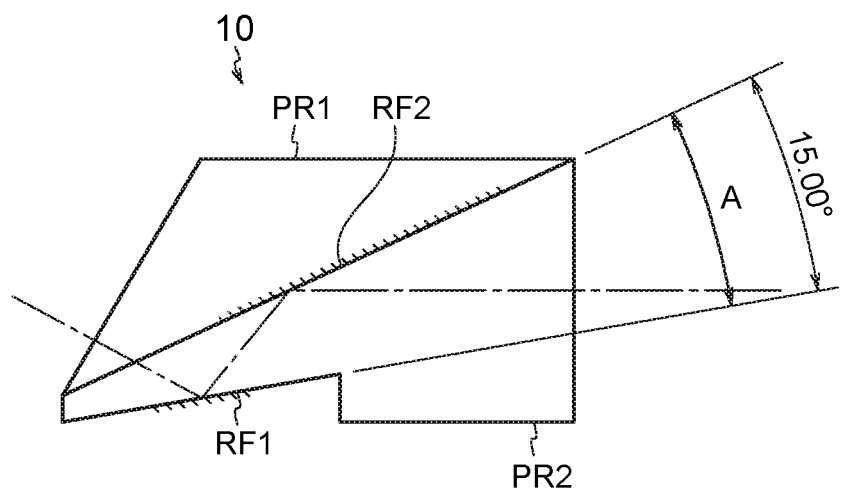

When conditional expression (1) is satisfied, in a case in which the first angle A=15° (FIG. 3B) for example, it is possible to pass a thick light beam of an endoscope optical system with a large NA (a large numerical aperture, NA) through the optical path deflecting prism for endoscope 10 without an occurrence of vignetting.

When a value falls below a lower limit value of conditional expression (1), in a case in which the first angle A=12° (FIG. 3B) for example, or more specifically, when the first angle A made by the first reflecting surface RF1 and the second reflecting surface RF2 is adjusted to 12° on a premise of not changing a path length in glass of the optical path deflecting prism for endoscope 10 and be constant as it has been, an optical axis transmitted through the first polished surface 11a is drawn excessively toward an edge portion. Consequently, vignetting of a light ray occurs in the optical path deflecting prism for endoscope 10.

Figure 3C:
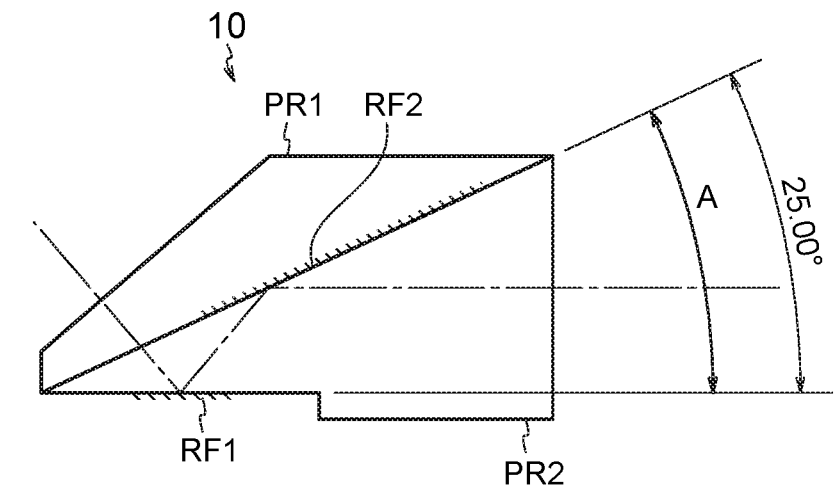

When an upper limit value of conditional expression (1) is exceeded, in a case in which the first angle A=25° (FIG. 3C) for example, or more specifically, when the first angle A made by the first reflecting surface RF1 and the second reflecting surface RF2 is adjusted to 25° on a premise of not changing the path length in glass of the optical path deflecting prism for endoscope 10, a distance between a point through which the optical axis passes through the third polished surface 11c and a point at which the optical axis is reflected at the third polished surface 11c becomes excessively close. Consequently, in the optical path deflecting prism for endoscope 10, overlapping of light beams occurs and as a result, the vignetting of the light ray occurs.

Moreover, it is desirable that the present embodiment satisfies conditional expression (2). Conditional expression (2) regulates an appropriate range of the second angle B.

Figure 4A:
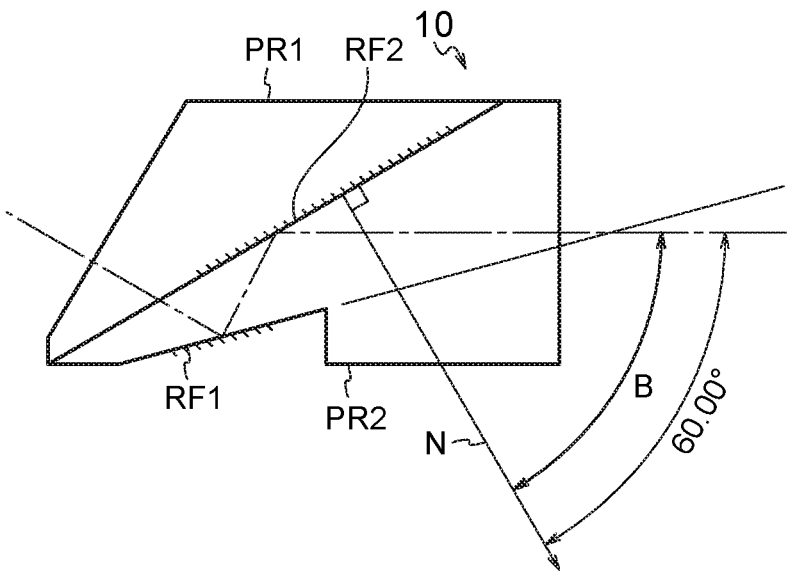
FIG. 4A, FIG. 4B, and FIG. 4C are other cross-sectional views of the optical path deflecting prism according to the first embodiment.
Figure 4B:
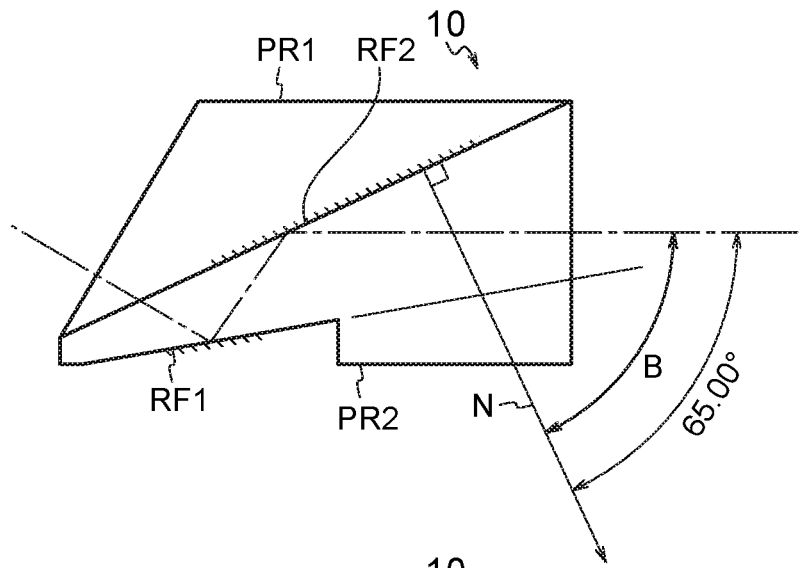

When conditional expression (2) is satisfied, in a case in which the second angle B=65° for example (FIG. 4B), it is possible to pass a thick light beam of the endoscope optical system with a large NA through the optical path deflecting prism for endoscope 10 without an occurrence of vignetting.

When a value falls below a lower limit value of conditional expression (2), in a case in which the second angle B=60° for example (FIG. 4A), or more specifically, when the second angle B made by the normal N direction of the second reflecting surface RF2 and the direction of the optical axis AX2 of the lens group 100 disposed on the emergence side of a light ray of the optical-axis deflecting prism for endoscope 10 (FIG. 2) is adjusted to 60° on a premise of not changing a path length in glass of the optical path deflecting prism for endoscope 10, a distance between a point through which the optical axis passes through the third polished surface 11c and a point at which the optical axis is reflected at the third polished surface 11c becomes excessively close. In the optical path deflecting prism for endoscope 10, as a result of an occurrence of overlapping of light beams, the vignetting of the light ray occurs.

Figure 4C:
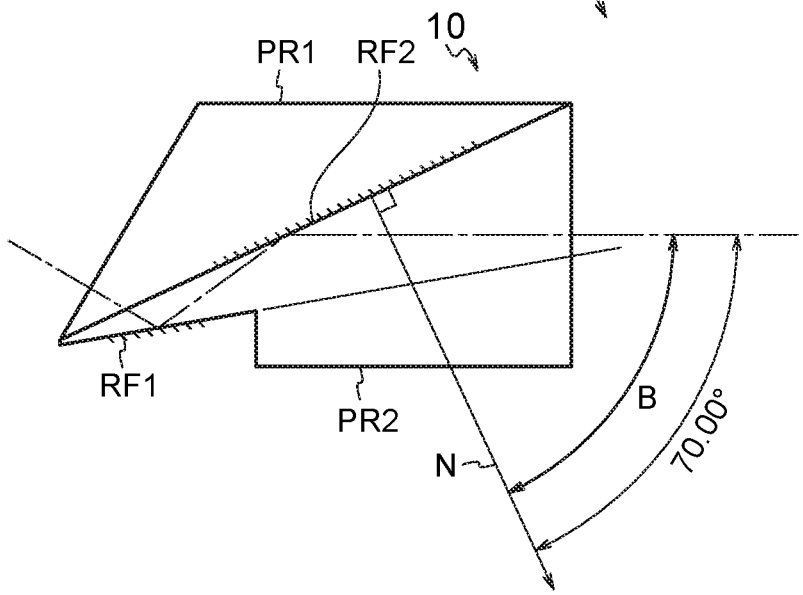

When an upper limit value of conditional expression (2) is exceeded, in a case in which the second angle B=70° for example (FIG. 4C), or more specifically, when the second angle B made by the normal N direction of the second reflecting surface RF2 and the direction of the optical axis AX2 of the lens group disposed on the emergence side of a light ray of the optical path deflecting prism 10 for endoscope is adjusted to 70° on a premise of not changing the path length in glass of the optical path deflecting prism for endoscope 10, an optical axis transmitted through the first polished surface 11a is drawn excessively toward the edge portion. Consequently, vignetting of a light ray occurs in the optical path deflecting prism for endoscope 10.

Second Embodiment

Figure 5A:
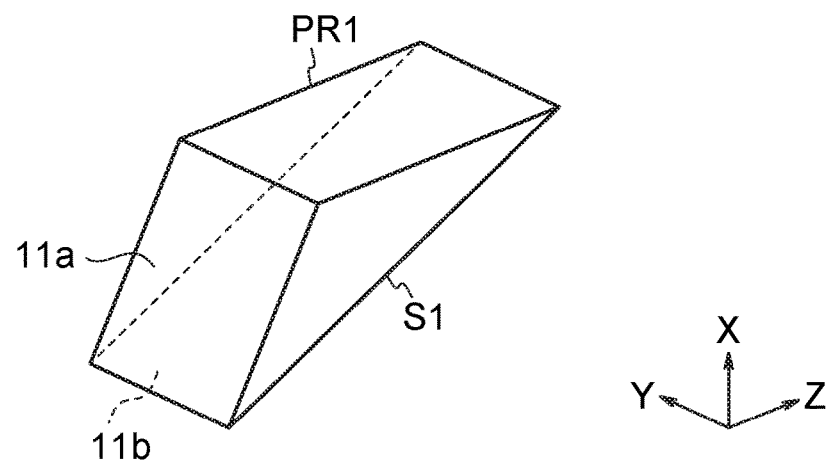
FIG. 5A is a perspective view of a first prism in an optical path deflecting prism for endoscope according to a second embodiment.
Figure 5B:
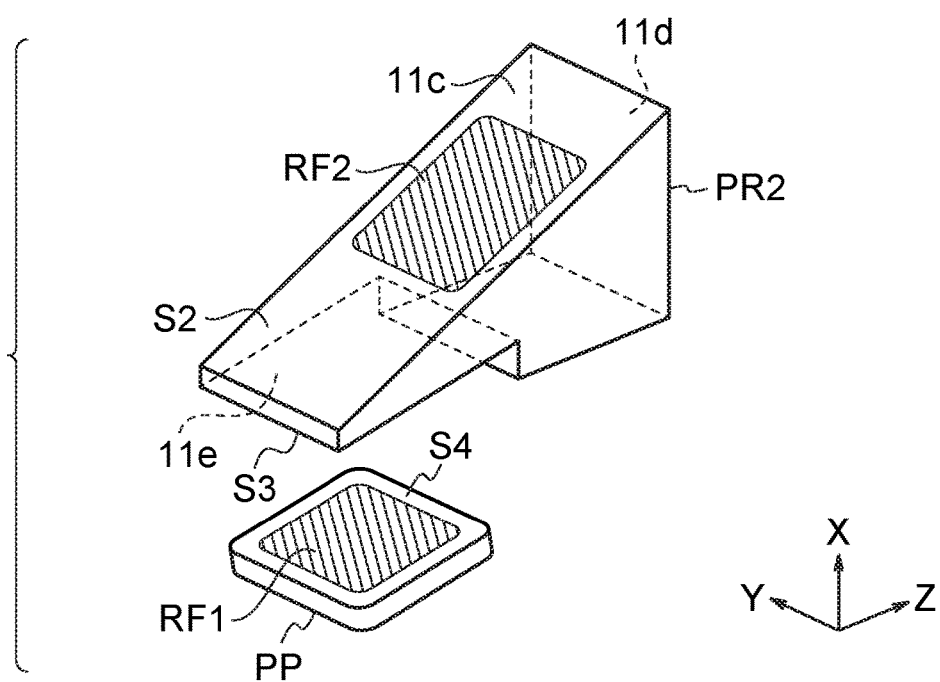
FIG. 5B is a perspective view of a second prism in the optical path deflecting prism for endoscope according to the second embodiment.
Figure 5C:
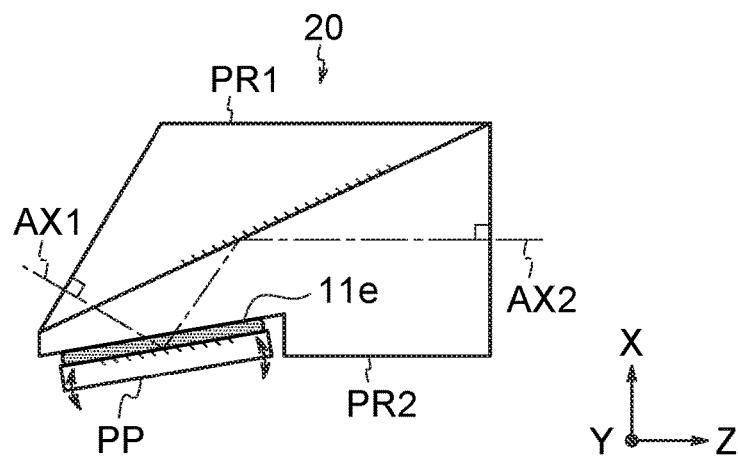
FIG. 5C is a cross-sectional view of the optical path deflecting prism for endoscope according to the second embodiment.

FIG. 5A is a perspective view of a first prism in an optical path deflecting prism for endoscope 20 according to a second embodiment. FIG. 5B is a perspective view of a second prism in the optical path deflecting prism for endoscope 20 according to the second embodiment. FIG. 5C is a cross-sectional view of the optical path deflecting prism for endoscope 20 according to the second embodiment. Same reference numerals are assigned to components that are same as in the first embodiment, and repetitive description thereof is omitted.

Moreover, in the optical path deflecting prism for endoscope 20 according to the present embodiment, it is desirable that the first reflecting surface RF1 is a mirror surface having a mirror coating applied to a polished surface of a plane parallel plate PP, and is fixed by gluing on the fifth polished surface 11e of the second prism PR2 upon adjusting an angle so as to correct an optical-axis shift which occurs due to a manufacturing error of the first prism PR1 and the second prism PR2.

As shown in FIG. 5B, a surface S3 of the second prism PR2 and a surface S4 of the plane parallel plate PP are cemented. The first reflecting surface RF1 is formed on a cemented-side surface of the plane parallel plate PP.

As shown in FIG. 5C, the first reflecting surface RF1 formed on the plane parallel plate PP is cemented to the fifth polished surface 11e after having adjusted the angle to cancel the manufacturing error of the first prism PR1 and the second prism PR2. A process for cementing the plane parallel plate PP after adjusting the angle will be described later.

Example 1

Figure 6:
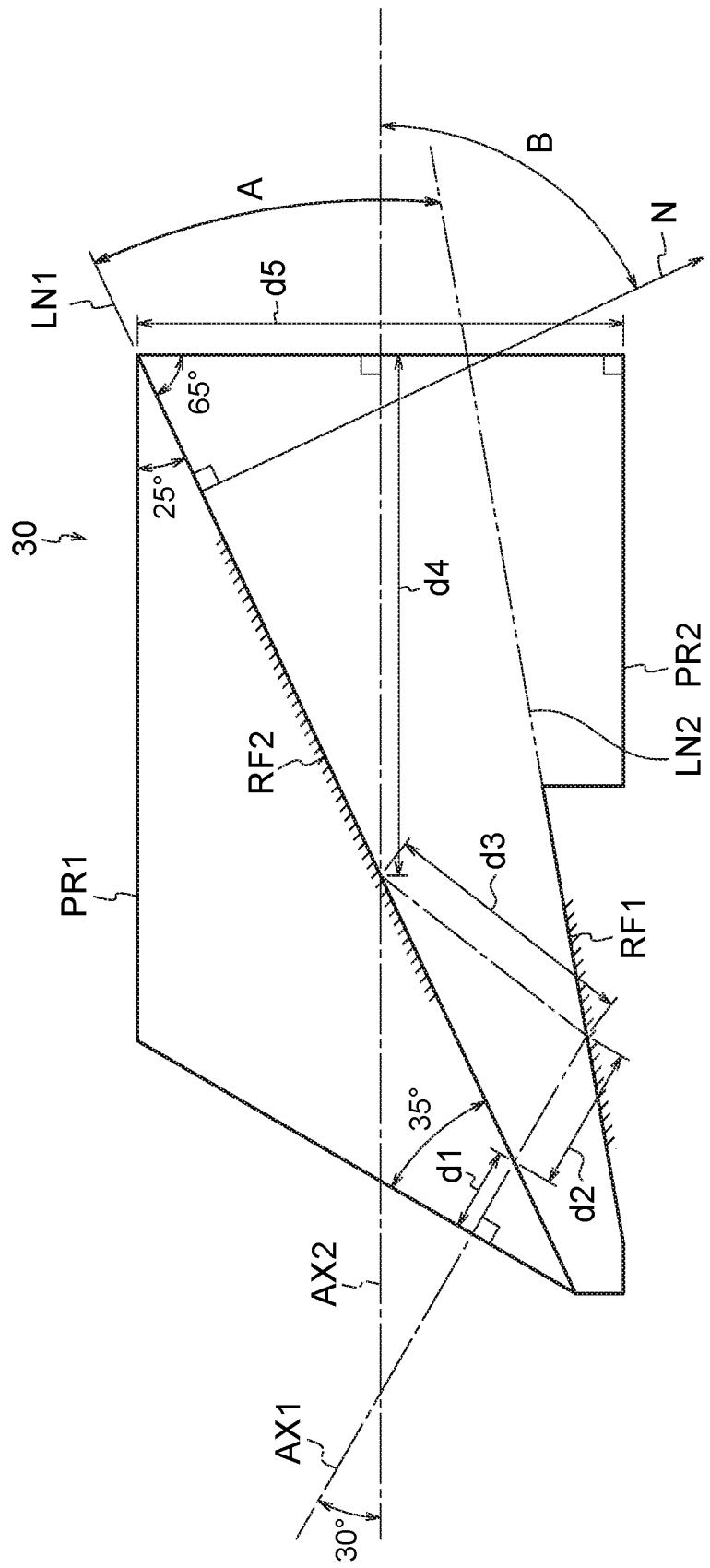
FIG. 6 is a cross-sectional view of an optical path deflecting prism for endoscope according to an example 1.

FIG. 6 is a cross-sectional view of an optical path deflecting prism for endoscope 30 according to an example 1. In diagrams of other examples, a straight line which is an elongation of a second reflecting surface RF2 is LN1. A straight line which is an elongation of a first reflecting surface RF1 is LN2.

Various data for the present example is shown below.
refractive index n for a d-line of a first prism PR1 and a second prism PR2 is, n=1.88
first angle A 15°
second angle B 65°
length d1=1.45
length d2=2.11
length d3=4.09
length d4=8.04
length d5=7.50
Each angle is shown in the diagram.

The present example satisfies conditional expressions (1) and (2). Moreover, with such configuration, even a thick light beam of an endoscope objective optical system with a high NA can also be transmitted through without an occurrence of vignetting.

Consequently, it is possible to provide a high-quality optical path deflecting prism for endoscope and an oblique-viewing endoscope optical system having a high NA.

Example 2

Figure 7:
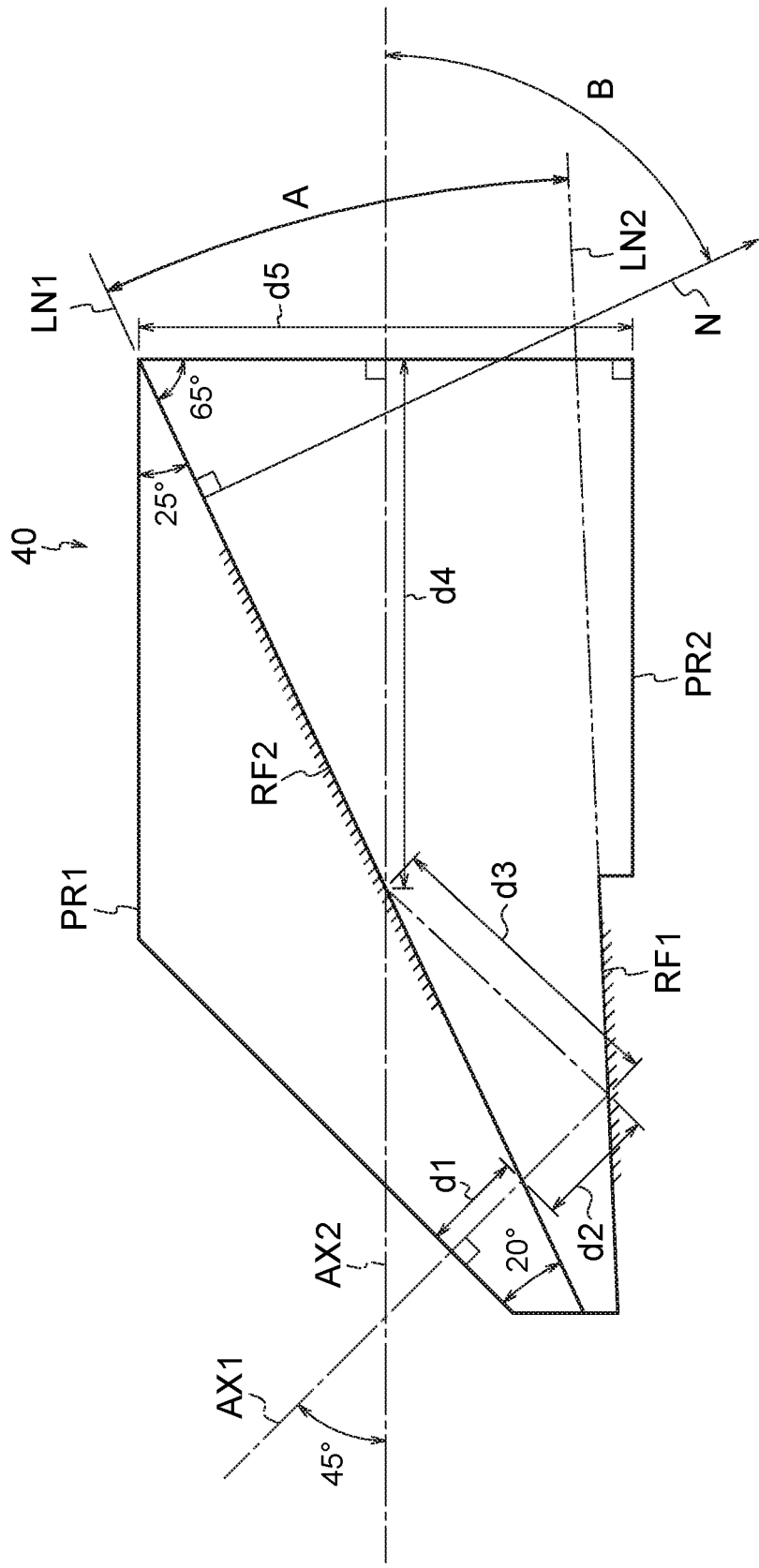
FIG. 7 is cross-sectional view of an optical path deflecting prism for endoscope according to an example 2.

FIG. 7 is a cross-sectional view of an optical path deflecting prism for endoscope 40 according to an example 2.
Various data of the present example is shown below.
refractive index n for a d-line of a first prism PR1 and a second prism PR2 is, n=1.88
first angle A 22.5°
second angle B 65°
length d1=1.33
length d2=1.93
length d3=4.36
length d4=8.07
length d5=7.50
Each angle is shown in the diagram.

The present example satisfies conditional expressions (1) and (2). Moreover, with such configuration, even a thick light beam of an endoscope optical system with a high NA can also be transmitted through without an occurrence of vignetting. Consequently, it is possible to provide a high-quality optical path deflecting prism for endoscope and an oblique-viewing endoscope optical system having a high NA.

Example 3

Figure 8:
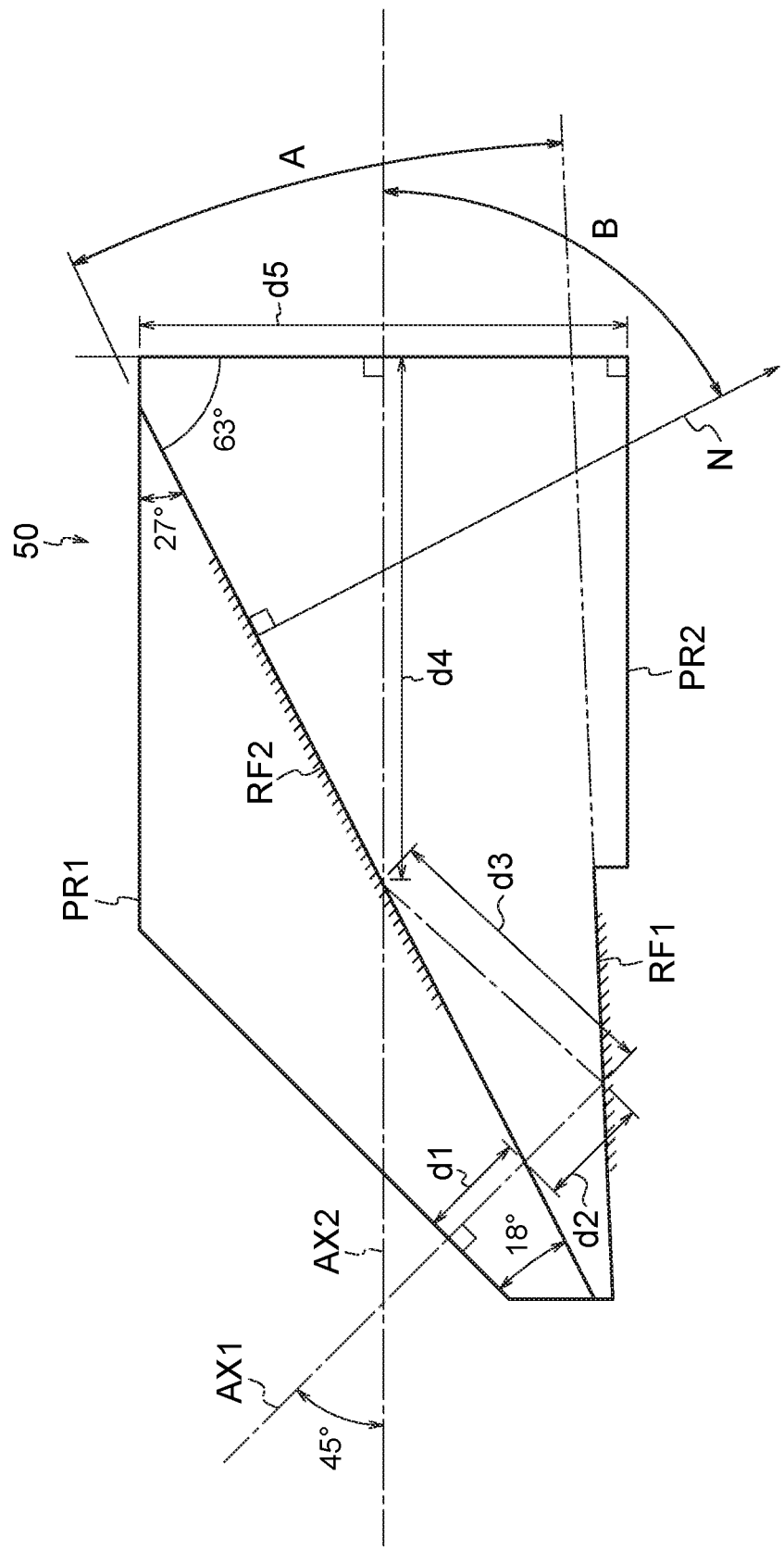
FIG. 8 is a cross-sectional view of an optical path deflecting prism for endoscope according to an example 3.

FIG. 8 is a cross-sectional view of an optical path deflecting prism for endoscope 50 according to an example 3.
Various data of the present example is shown below.
refractive index n for a d-line of a first prism PR1 and a second prism PR2 is, n=1.88
first angle A 22.5°
second angle B 65°
length d1=1.61
length d2=1.94 length d3=4.10
length d4=8.04
length d5=7.50
Each angle is shown in the diagram.

The present example satisfies conditional expressions (1) and (2). Moreover, with such configuration, even a thick light beam of an endoscope optical system with a high NA can also be transmitted through without an occurrence of vignetting. Consequently, it is possible to provide a high-quality optical path deflecting prism for endoscope and an oblique-viewing endoscope optical system having a high NA.

Example 4

Figure 9A:
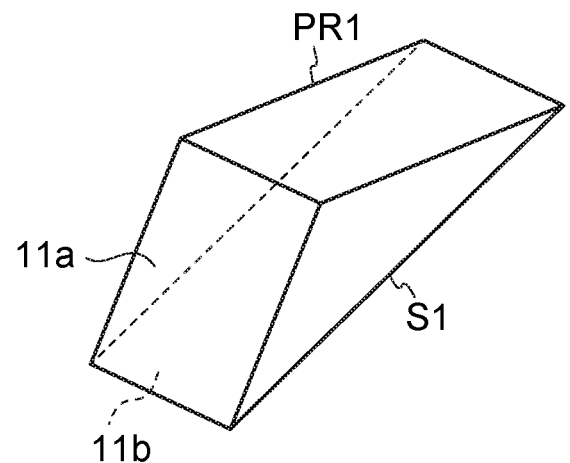
FIG. 9A is a perspective view of a first prism in an optical path deflecting prism for endoscope according to an example 4.
Figure 9B:
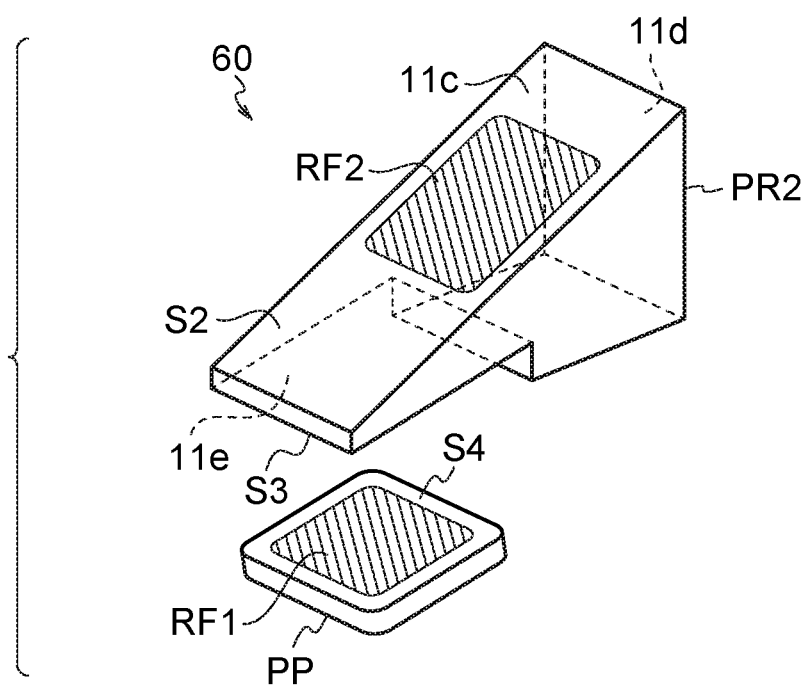
FIG. 9B is a perspective view of a second prism in the optical path deflecting prism for endoscope according to the example 4.

FIG. 9A is a perspective view of a cemented state of a first prism PR1 and a second prism PR2 in an optical path deflecting prism for endoscope 60 according to an example 4, and FIG. 9B is a perspective
view of the second prism PR2 in the optical path deflecting prism for endoscope 60 according to the example 4.

In the present example, a first reflecting surface RF1 is a mirror surface having a mirror coating applied to a polished surface formed on the plane parallel plate PP. The first reflecting surface RF1 formed on the plane parallel plate PP is cemented to a fifth polished surface 11e after having adjusted the angle to cancel the manufacturing error of the first prism PR1 and the second prism PR2. A process for cementing the plane parallel plate PP after adjusting the angle will be described later.

Figure 10A:
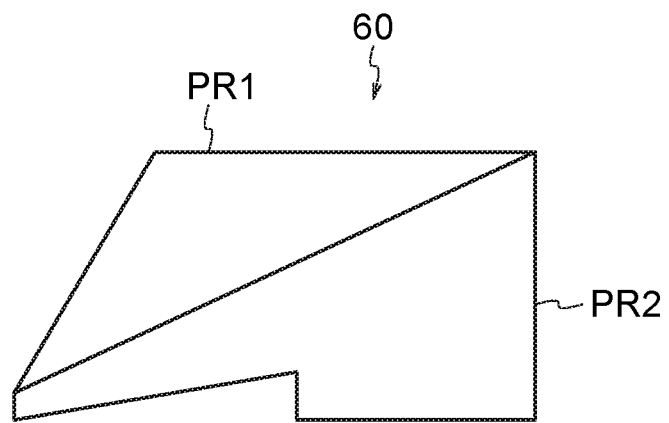
FIG. 10A is a cross-sectional view of a cemented state of the first prism and the second prism in the optical path deflecting prism for endoscope according to the example 4.
Figure 10B:
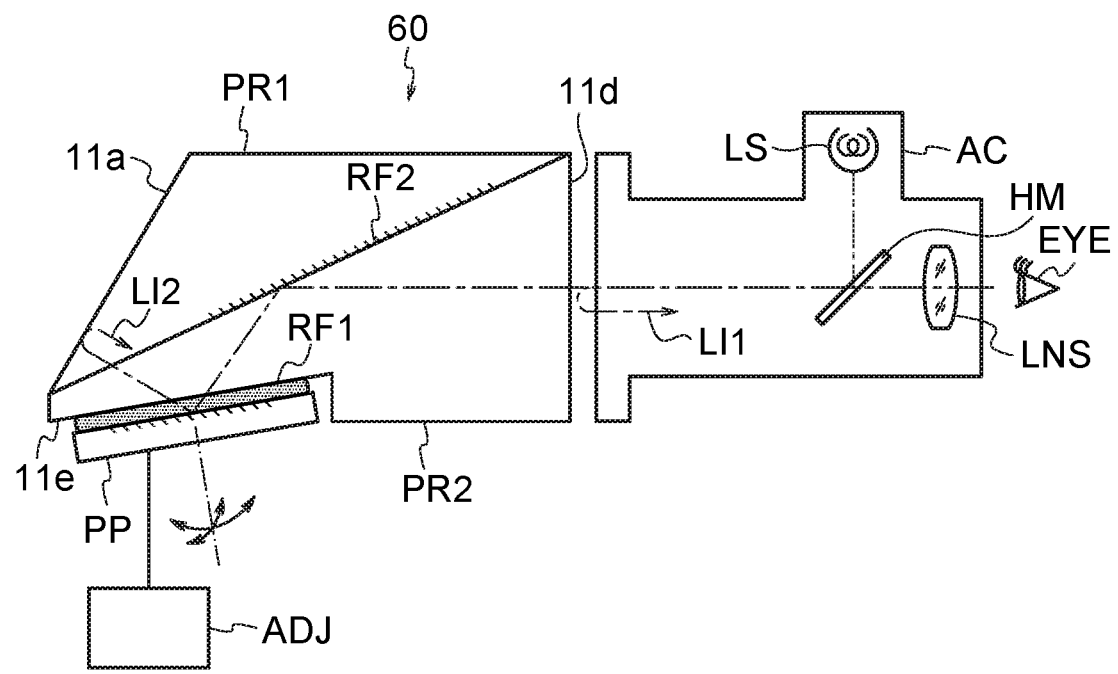
FIG. 10B is a diagram showing an arrangement for adjusting the optical path deflecting prism for endoscope according to the example 4.

FIG. 10A is a cross-sectional view of the cemented state of the first prism PR1 and the second prism PR2 in the optical path deflecting prism for endoscope 60 according to an example 4. FIG. 10B is a diagram showing an arrangement for adjusting the optical path deflecting prism for endoscope 60 according to the example 4.

In FIG. 10B, an adjustment at the time of gluing the plane and parallel plate PP will be described. By using an auto-collimator AC, an adjustment of tilting of the plane parallel plate PP is carried out so that, return light LI2 from a first polished surface 11a and return light LI1 from a fourth polished surface 11d are aligned. An angle adjuster ADJ carries out an adjustment of angle (adjustment of tilting) of the plane parallel plate PP. Moreover, in a state of the return lights LI1 and LI2 aligned, the plane parallel plate PP is cemented to a fifth polished surface 11e. Accordingly, it is possible to cancel the manufacturing error of the first prism PR1 and the second prism PR2.

Figure 11A:
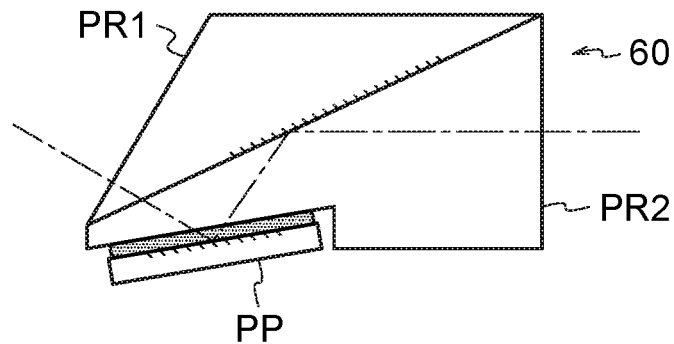
FIG. 11A is a cross-sectional view of an arrangement of the optical path deflecting prism for endoscope according to the example 4.
Figure 11B:
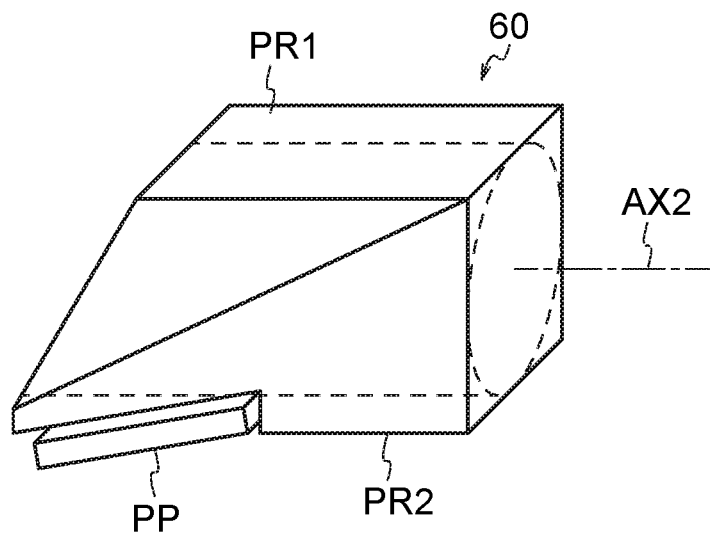
FIG. 11B is a perspective view of the arrangement of the optical path deflecting prism for endoscope according to the example 4.
Figure 11C:
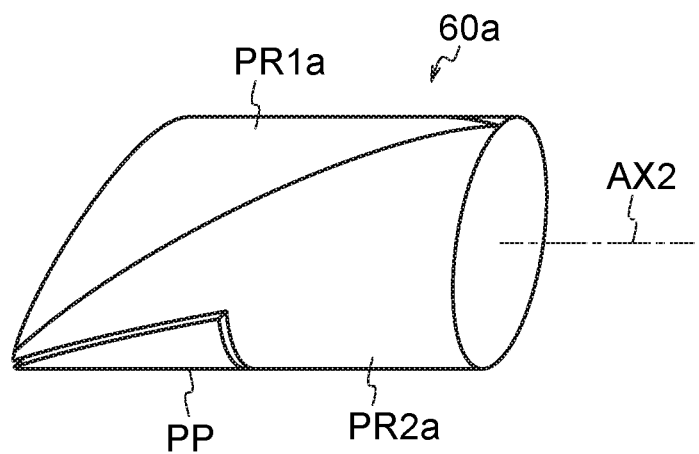
FIG. 11C is a perspective view in which the optical path deflecting prism for endoscope according to the example 4 is processed to have a circular cylindrical shape.

FIG. 11A is a cross-sectional view of the optical path deflecting prism for endoscope 60 according to the example 4 obtained through the abovementioned process. FIG. 11B is a perspective view of the optical path deflecting prism for endoscope 60 according to the example 4. FIG. 11C is a perspective view in which the optical path deflecting prism for endoscope 60 according to the example 4 is processed to a circular cylindrical shape.

The optical path deflecting prism for endoscope 60 is cut to a circular cylindrical shape having a desired radius indicated by dashed lines in FIG. 11B. FIG. 11C shows an optical path deflecting prism for endoscope 60a which has assumed a circular cylindrical shape after cutting.

More specifically, the optical path deflecting prism for endoscope 60a is circular cylindrical shaped, having a first prism PR1a, a second prism PR2a, and a plane parallel plate PP.

Figure 12A:
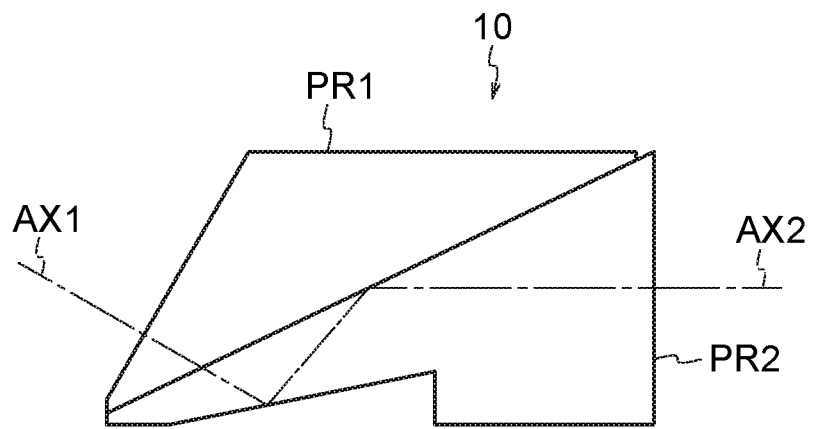
FIG. 12A is a cross-sectional view of an arrangement of the optical path deflecting prism for endoscope according to the first embodiment.
Figure 12B:
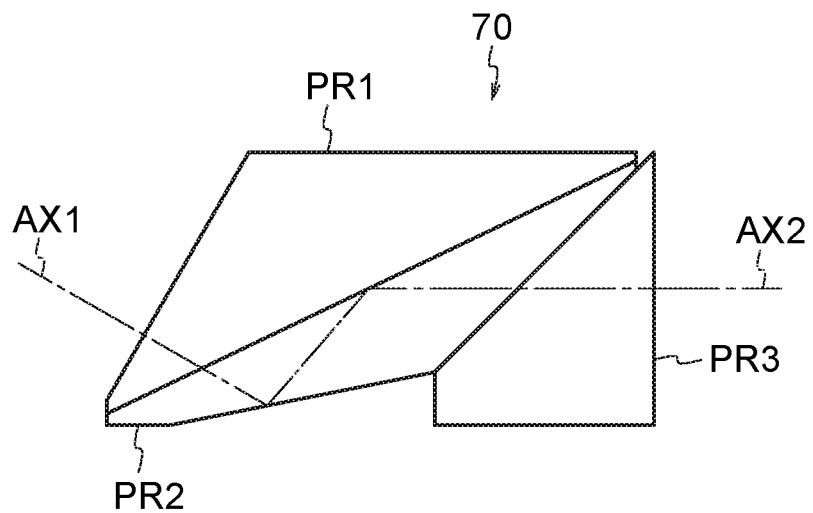
FIG. 12B is a cross-sectional view of an arrangement of an optical path deflecting prism for endoscope according to a modified example.

FIG. 12A is a cross-sectional view of an arrangement of the optical path deflecting prism 10 according to the abovementioned example for instance. In the examples, an optical path deflecting prism for endoscope 70 is formed by gluing two prisms. However, without restricting to such arrangement, it is possible to form the optical path deflecting prism for endoscope 70 by cementing the first prism PR1, a second prism PR2, and a third prism PR3.

Example 5

Moreover, an oblique-viewing endoscope optical system according to the present embodiment, according to another aspect of the present disclosure, includes the abovementioned optical path deflecting prism for endoscope, and an optical system which is disposed on the emergence side of the optical path deflecting prism for endoscope.

Figure 13:
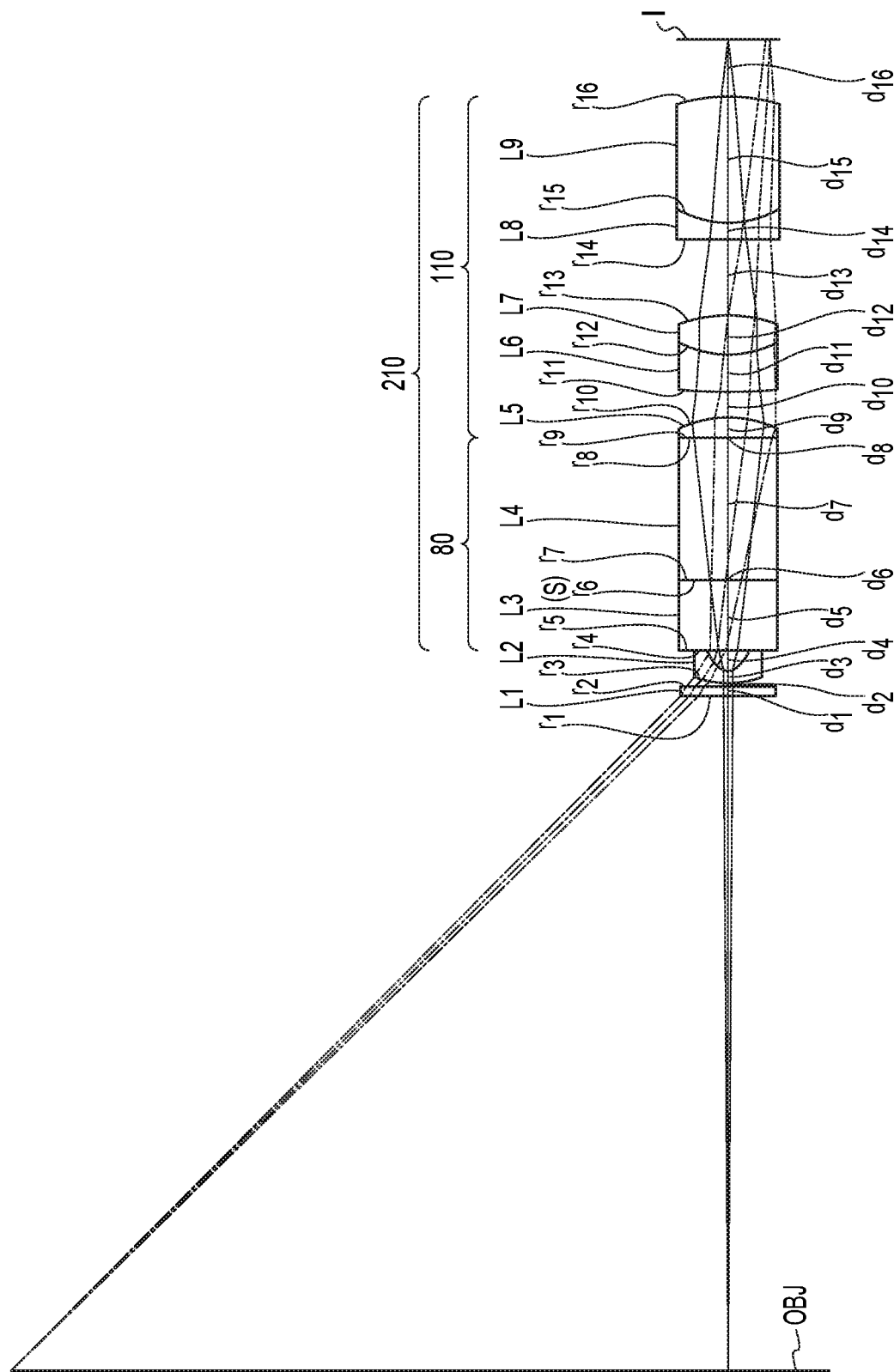
FIG. 13 is a cross-sectional view of a lens arrangement in an oblique-viewing endoscope optical system according to an example 5.

FIG. 13 is a cross-sectional view of a lens arrangement of an oblique-viewing endoscope optical system 210 according to an example 5. The oblique-viewing endoscope optical system 210 includes an optical path deflecting prism for endoscope 80, and a lens group 110.

The oblique-viewing endoscope optical system 210 includes in order from an object side, a plane parallel plate L1, a negative meniscus lens L2 having a convex surface directed toward the object side, the optical path deflecting prism for endoscope 80, and the lens group 110. In the cross-sectional view of the lens arrangement, the optical path deflecting prism for endoscope 80 is shown as a rectangular parallelepiped body in an unfolded state. A planoconvex lens L5 having a flat surface directed toward the object side is cemented to an image-side surface of the optical path deflecting prism for endoscope 80. The lens group 110 further includes in order from the object side, a negative meniscus lens L6 having a convex surface directed toward the object side, a biconvex positive lens L7, a planoconvex positive lens L8 having a flat surface directed toward the object side, and a biconvex positive lens L9. In order from the object side, the negative meniscus lens L6 and the biconvex positive lens L7 are cemented. The planoconvex positive lens L8 and the biconvex positive lens L9 are cemented. An
imaging plane (image pickup surface) I is on an image side of the lens group 110.

Numerical data for each example is shown below. In surface data, r denotes a radius of curvature of each lens surface, d denotes a distance between two lens surfaces, nd denotes a refractive index for a d-line of each lens, and vd denotes Abbe's number for each lens. S denotes an aperture stop. ER denotes an effective diameter.

Moreover, an aspheric surface shape is expressed by the following expression when z is an optical axial direction, y is a direction orthogonal to an optical axis, k is a conical coefficient, and A4, A6, A8, and A10 are aspherical coefficients.

$$Z=(y^2/r)/[1+\{1-(1+k)(y/r)^2\}^{1/2}]+A4y^4+A6y^6+A8y^8+A10y^{10}$$

Example 1

| Unit mm | | | | | |
|---|---|---|---|---|---|
| Surface data | | | | | |
| Surface no. | r | d | nd | vd | ER |
| Object plane | ∞ | 50 | | | 106.314 |
| 1 | ∞ | 0.7 | 1.769000 | 64.150000 | 7 |
| 2 | ∞ | 0.2 | | | 7 |
| 3* | 4.522 | 1 | 1.807260 | 40.720000 | 5.1 |

-continued

Unit mm

| | | | | | |
|---|---|---|---|---|---|
| 4* | 0.979 | 1.52 | | | 3.2 |
| 5 | ∞ | 5.25 | 1.882997 | 40.765107 | 7.3 |
| 6 (Stop) | ∞ | 0 | | | 2.6 |
| 7 | ∞ | 10.44 | 1.882997 | 40.765107 | 7.3 |
| 8 | ∞ | 0 | | | 7.3 |
| 9 | ∞ | 1.56 | 1.884480 | 40.600000 | 7.3 |
| 10* | −7.346 | 1.92 | | | 7.3 |
| 11 | 32.789 | 2.7 | 1.862900 | 24.800000 | 7 |
| 12 | 7.854 | 3 | 1.439860 | 94.660000 | 7.3 |
| 13 | −9.813 | 5.55 | | | 7.3 |
| 14 | ∞ | 1.2 | 1.647689 | 33.792803 | 7.5 |
| 15 | 7.427 | 9.3 | 1.439860 | 94.660000 | 7.5 |
| 16 | −13.117 | 4.144 | | | 7.5 |
| 17 | ∞ | 0 | | | 6.217315 |
| Image pickup surface | ∞ | | | | 6.217315 |

Aspherical surface data

3rd surface k = −0.637
A4 = −0.005835, A6 = 0.0001631

4th surface k = −0.827
A4 = 0.004699, A6 = −0.004477

10th surface k = −0.378
A4 = 0.0001792

As mentioned above, it is possible to provide an oblique-viewing endoscope (endoscope) having installed an optical path deflecting prism for endoscope which does not allow vignetting of a light beam, a flare, and a ghost to occur even in an endoscope in which the numerical aperture is made high. Moreover, it is possible to provide an inexpensive oblique-viewing endoscope optical system having an inexpensive optical path deflecting prism for endoscope by providing an angle adjuster to one of reflecting surfaces of an optical path deflecting prism group for correcting an optical-path shift which occurs due to a manufacturing error (an angle error) of a prism in the optical path deflecting prism for endoscope.

Various embodiments of the present invention were described above. However, the present invention is not restricted only to the embodiments described heretofore, and embodiments in which the arrangements of these embodiments are appropriately combined without departing from the scope of the invention, are also within the scope of the present invention.

(Note)

A disclosure of the following arrangements is derived from the examples described heretofore.

(Appended Mode 1)

It is possible to obtain the abovementioned optical path deflecting prism for endoscope by a method of manufacturing as follows.

A method of manufacturing an optical path deflecting prism for endoscope for observing an object in an oblique direction, comprising steps of:

cementing a first prism and a second prism of the optical path deflecting prism for endoscope;
forming a first polished surface which is perpendicular to the oblique direction, and the first polished surface is a first light-beam incident surface for light incident on the optical path deflecting prism for endoscope, in the first prism;
forming a second polished surface which is disposed at an angle with respect to the first polished surface, and the second polished surface is a cemented surface with the second prism;
forming a third polished surface which is a cemented surface with the first prism;
forming a fourth polished surface which is perpendicular to an optical axis of a lens group disposed on an emergence side of the optical path deflecting prism for endoscope, and the fourth polished surface is a last light-beam emergence surface for light emerged from the optical path deflecting prism for endoscope;
forming a fifth polished surface which is disposed at an angle with respect to the third polished surface;
making a first reflecting surface which reflects first time a light beam incident on the optical path deflecting prism for endoscope exist on the fifth polished surface of the second prism; and
making a second reflecting surface which reflects second time a light beam incident on the optical path deflecting prism for endoscope exist on any one of the second polished surface of the first prism and the third polished surface of the second prism, wherein
t the following conditional expressions (1) and (2) are satisfied, $$14.5 \leq A(°) \leq 23 \quad (1)$$

$$62 \leq B(°) \leq 66 \quad (2)$$

where,
A denotes a first angle made by the first reflecting surface and the second reflecting surface with each other, and
B denotes a second angle made by a normal direction of the second reflecting surface and an optical axial direction of a lens group disposed on an emergence side of a light beam of the optical path deflecting prism for endoscope.

As described heretofore, the present disclosure is suitable for an optical path deflecting prism for endoscope which does not allow a ghost, a flare, and a vignetting of a light beam even in an endoscope in which the numerical aperture NA is made high, and an oblique-viewing endoscope optical system having the optical path deflecting prism for endoscope, and an endoscope.

According to the present disclosure, it is possible to provide an optical path deflecting prism for endoscope which does not allow a ghost, a flare, and a vignetting of a light beam even in an endoscope in which the numerical aperture NA is made high, and an oblique-viewing endoscope optical system having the optical path deflecting prism for endoscope, and an endoscope.

What is claimed is:

1. An optical path deflecting prism comprising:
a first prism; and
a second prism,
wherein:
the first prism and the second prism are cemented,
the first prism has a first polished surface and a second polished surface,
the first polished surface is perpendicular to an oblique direction and has a first light-beam incident surface for light incident on the optical path deflecting prism,
the second polished surface is disposed at an angle with respect to the first polished surface, and is a cemented surface with the second prism,
the second prism has a third polished surface, a fourth polished surface, and a fifth polished surface, the third polished surface is a cemented surface with the first prism, the fourth polished surface is perpendicular to an optical axis on an emergence side of the optical path deflecting prism, and is a last light-beam emergence surface for light emerged from the optical path deflecting prism, the fifth polished surface is disposed at an angle with respect to the third polished surface, a first reflecting surface reflects a first time, a light beam incident on the optical path deflecting prism, and exists on the fifth polished surface of the second prism, a second reflecting surface reflects a second time, a light beam incident on the optical path deflecting prism, and exists on any one of the second polished surface of the first prism and the third polished surface of the second prism, the first reflecting surface is a mirror surface having a mirror coating applied to a polished surface of a flat plate, and the first reflecting surface is fixed by gluing to the fifth polished surface of the second prism upon adjusting an angle so as to correct an optical-axis shift which occurs due to a manufacturing error of the first prism and the second prism, and the following conditional expressions (1) and (2) are satisfied:

$$14.5 \leq A(°) \leq 23 \quad (1), \text{and}$$

$$62 \leq B(°) \leq 66 \quad (2),$$

where:

A denotes a first angle made by the first reflecting surface and the second reflecting surface with each other, and B denotes a second angle made by a normal direction of the second reflecting surface and an optical axial direction of the optical axis on the emergence side of the optical path deflecting prism.

2. An oblique-viewing endoscope optical system comprising:

the optical path deflecting prism according to claim 1; and an optical system which is disposed on the emergence side of the optical path deflecting prism.

3. An endoscope comprising:

the oblique-viewing endoscope optical system according to claim 2.

* * * * *